US011959344B2

(12) United States Patent
Cobb

(10) Patent No.: US 11,959,344 B2
(45) Date of Patent: *Apr. 16, 2024

(54) AUTOMATED REMOTE LINE MAINTENANCE AND SAMPLE CONDITIONING SYSTEM

(71) Applicant: Reservoir Group Inc., Stafford, TX (US)

(72) Inventor: Isaac David Cobb, Tomball, TX (US)

(73) Assignee: Reservoir Group, Inc., Staffford, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/086,111

(22) Filed: Dec. 21, 2022

(65) Prior Publication Data

US 2023/0127365 A1    Apr. 27, 2023

Related U.S. Application Data

(63) Continuation of application No. 17/069,199, filed on Oct. 13, 2020, now Pat. No. 11,536,102.

(60) Provisional application No. 62/914,590, filed on Oct. 14, 2019.

(51) Int. Cl.
| *E21B 49/08* | (2006.01) |
| *E21B 21/06* | (2006.01) |
| *G01N 33/28* | (2006.01) |
| *E21B 47/26* | (2012.01) |

(52) U.S. Cl.
CPC ............ *E21B 21/067* (2013.01); *E21B 49/08* (2013.01); *G01N 33/2823* (2013.01); *E21B 47/26* (2020.05)

(58) Field of Classification Search
CPC ........ E21B 21/067; E21B 49/08; E21B 47/26; G01N 33/2823
See application file for complete search history.

(56) References Cited

U.S. PATENT DOCUMENTS

| 4,402,910 | A  | 9/1983  | Smith et al. |
| 6,666,099 | B2 | 12/2003 | Taylor |
| 9,244,047 | B2 | 1/2016  | Selman et al. |
| 9,442,218 | B2 | 9/2016  | Selman et al. |
| 10,125,557 | B2 | 11/2018 | Shanks et al. |
| 2014/0088874 | A1 | 3/2014 | Selman |
| 2016/0047784 | A1 | 2/2016 | Bright |

*Primary Examiner* — Kristina M Deherrera
*Assistant Examiner* — Jean F Morello
(74) *Attorney, Agent, or Firm* — Stephen Y. Liu; Carstens, Allen & Gourley, LLP

(57) ABSTRACT

In an embodiment, a sample conditioning system includes a first valve subsystem, a controller, and a signal generator. The first valve subsystem includes a first electrically activated valve and a first timed switch in electrical communication with the first electrically activated valve, where the first timed switch is configured with a first time duration. The controller is configured to receive drilling data from a data source and, responsive to the drilling data satisfying a trigger associated with a timed sequence, cause the signal generator to apply a signal to at least the first timed switch. The signal causes the first timed switch to close for at least the first time duration and power the first electrically activated valve, the powered first electrically activated valve switching to allow air from a first air line to pass therethrough to a sample line.

19 Claims, 10 Drawing Sheets

AUTOMATED REMOTE LINE MAINTENANCE AND SAMPLE CONDITIONING SYSTEM

CROSS-REFERENCE TO RELATED APPLICATIONS

This patent application is a continuation of pending U.S. patent application Ser. No. 17/069,199, filed on Oct. 13, 2020, which claims priority from U.S. Provisional Patent Application No. 62/914,590, filed on Oct. 14, 2019, of which are incorporated herein by reference in their entirety.

BACKGROUND

This section provides background information to facilitate a better understanding of the various aspects of the disclosure. It should be understood that the statements in this section of this document are to be read in this light, and not as admissions of prior art.

Unmanned remote mudlogging applications often run into issues involving the maintenance of chemicals and gas lines on unattended rig locations. In addition to destroying capital equipment, this issue results in unreliable gas curves and complete data loss for customers. Using too much "sample conditioning" creates unintended consequences including, but not limited to, adding excess volumes of void space, which allow gas sample to comingle for excessive periods of time before quantitative measurements are performed. Adding desiccants inline to prevent coalescing of moisture in sample lines creates surfaces for hydrocarbon residues to adhere to; furthermore, in unmanned applications, companies will utilize increased volumes of these desiccants to maximize unattended run times. Utilizing hydroscopic liquids similarly can lead to unintended associations of hydrocarbons in the drying liquid. Finally, as desiccants move toward exhaustion, they will lose their effectiveness and/or will change their physical nature, resulting in changing sample flow patterns.

An additional effect of unmanned processes involves accumulations of excess moisture in saddle points along a sample line, as well as refluxing of coalesced moisture in sections of sample line whose angle of incidence to a horizontal tangent surpasses a critical value. Over the length of a gas sample line these effects increasingly affect gas sample density and flow patterns. Adding numerous traditional "engineered" controls inline results in decreased efficacy of gas line(s) purging cycles. Importantly, purging lines with a reversed flow cycle can exacerbate the deterioration of chemicals. In some instances, reversed flow may not even be possible because of these inline "controls" and doing so may result in a gas line failure. p One final step often taken in remote applications to remove moisture from gas samples is refrigeration. Refrigeration is an effective means of water removal; however, it also effectively removes heavier hydrocarbon residues, which may have made it beyond all other "engineered" controls. By refrigerating a sample, a company essentially removes the majority of hydrocarbons, or chemicals of interest, whose boiling point is above ~35° Fahrenheit, assuming an ideal refrigeration temperature for food is being utilized in a commercially available refrigerator unit. This effectively eliminates any detectable concentrations of hydrocarbons having more than four carbons in an unbranched chain, or five carbons in a branched chain.

Combined, these effects all lead to a less reliable data set, inefficient deployment of personnel to maintain gas lines made unreliable and additional costs of consumed and stocked chemicals to run these types of jobs.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In an embodiment, a sample conditioning system includes a first valve subsystem configured to receive sample via a sample line from a sample source to a sample detector. The first valve subsystem includes a first electrically activated valve and a first timed switch in electrical communication with the first electrically activated valve, where the first timed switch is configured with a first time duration. The sample conditioning system also includes a signal generator in electrical communication with the first timed switch. The sample conditioning system also includes a controller communicably coupled to the signal generator. The controller is configured to receive drilling data from a data source. Responsive to the drilling data satisfying a trigger associated with a timed sequence, the controller is further configured to cause the signal generator to apply a signal to at least the first timed switch, the signal causing the first timed switch to close for at least the first time duration and power the first electrically activated valve, the powered first electrically activated valve switching to allow air from a first air line to pass therethrough to the sample line. Other embodiments of this aspect include corresponding computer systems, apparatus, and computer programs recorded on one or more computer storage devices, each configured to perform the actions of the methods.

In one general aspect, in an embodiment, a method of automating a sample conditioning system that includes a plurality of valves and a controller is performed by a controller. The method includes receiving drilling data from a data source. The method also includes, responsive to the drilling data satisfying a trigger associated with a timed sequence, causing a signal to be applied to at least a first timed switch, the signal causing the first timed switch to close for a first time duration and power a first electrically activated valve in a sample line. The powered first electrically activated valve switches to allow air from an air line to pass therethrough to the sample line. Other embodiments of this aspect include corresponding computer systems, apparatus, and computer programs recorded on one or more computer storage devices, each configured to perform the actions of the methods.

BRIEF DESCRIPTION OF THE DRAWINGS

A more complete understanding of the method and apparatus of the present disclosure may be obtained by reference to the following Detailed Description when taken in conjunction with the accompanying Drawings wherein.

DETAILED DESCRIPTION

Figure 1:
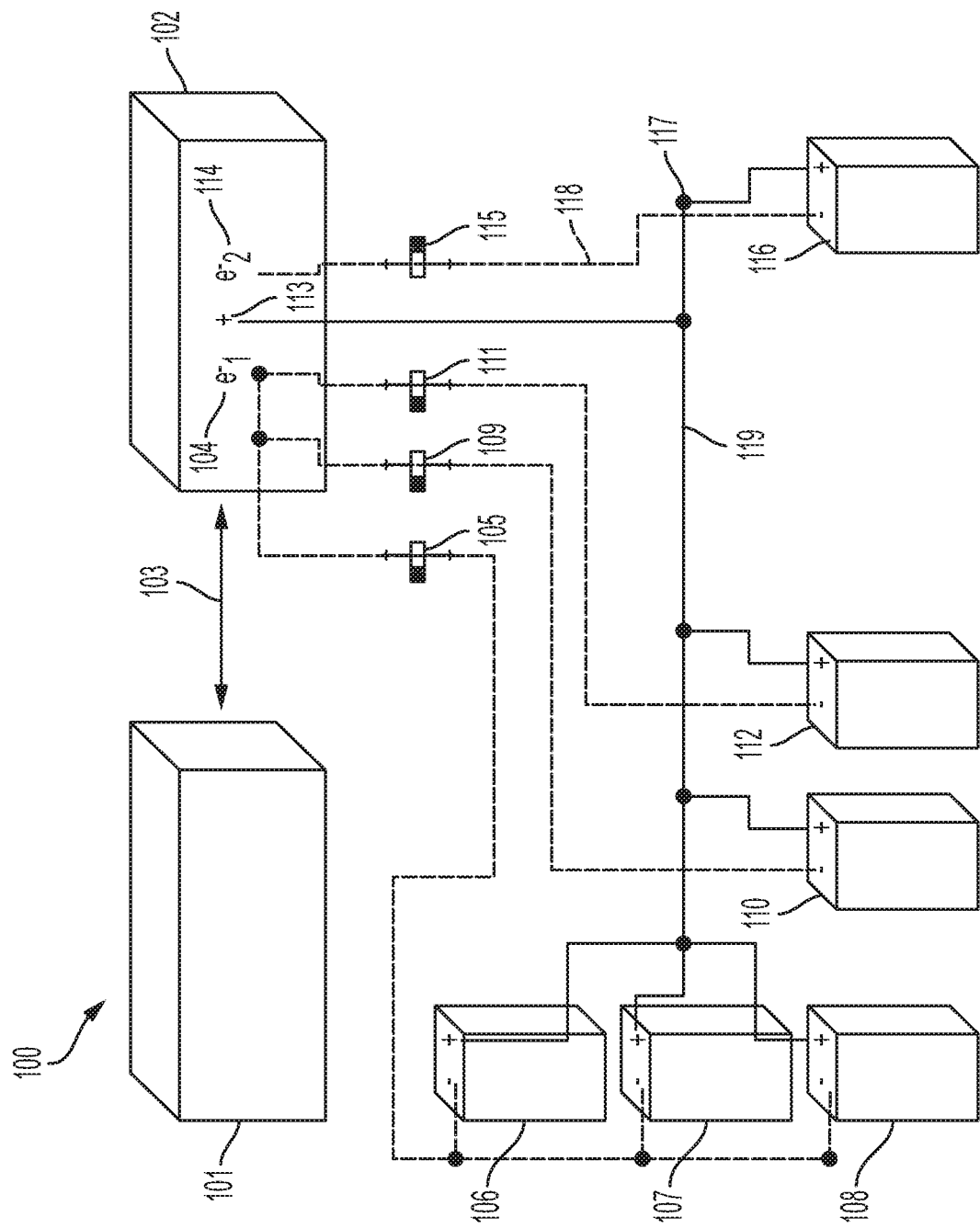
FIG. 1 illustrates an example of a system for signaling a start of a sequence.

It is to be understood that the following disclosure provides many different embodiments, or examples, for implementing different features of various illustrative embodiments. Specific examples of components and arrangements are described below to simplify the disclosure. These are, of course, merely examples and are not intended to be limiting. For example, a figure may illustrate an exemplary embodiment with multiple features or combinations of features that are not required in one or more other embodiments and thus a figure may disclose one or more embodiments that have fewer features or a different combination of features than the illustrated embodiment. Embodiments may include some but not all the features illustrated in a figure and some embodiments may combine features illustrated in one figure with features illustrated in another figure. Therefore, combinations of features disclosed in the following detailed description may not be necessary to practice the teachings in the broadest sense and are instead merely to describe particularly representative examples. In addition, the disclosure may repeat reference numerals and/or letters in the various examples. This repetition is for the purpose of simplicity and clarity and does not itself dictate a relationship between the various embodiments and/or configurations discussed.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include such elements or features.

As used herein, the terms "connect," "connection," "connected," "in connection with," and "connecting" may be used to mean in direct connection with or in connection with via one or more elements. Similarly, the terms "couple," "coupling," and "coupled" may be used to mean directly coupled or coupled via one or more elements. Terms such as "up," "down," "top," and "bottom" and other like terms indicating relative positions to a given point or element may be utilized to more clearly describe some elements. Commonly, these terms relate to a reference point such as the surface from which drilling operations are initiated.

The present disclosure describes examples of systematically caring for and maintaining sample quality coming to gas detectors in harsh environments. In such environments, steps must be taken to remove moisture and solid particulate material from bulk sample gases, most of which, will be exhausted back out to atmosphere. For example, in mud-logging, oftentimes, extended lines of polymer-comprised tubing are run across drilling locations. For safety, these lines must be run hanging overhead, around obstacles, and under assorted heavy equipment. These runs can become quite difficult to maintain, and even more difficult to rerun, should the need arise, during active drilling operations. In addition to being treacherous to run, the lines themselves create complicated undulations and saddle points that will collect moisture, which is eventually transported back to the detectors. Through simple routine maintenance the undulations and saddle points can be cleared of moisture, but too often this simple task is done too sporadically.

The present disclosure describes examples of adding a device or system to assist in sample conditioning and routine maintenance of sample lines, thereby allowing a mud logging company, for example, to ensure the integrity of its gas readings and safety of its equipment. In various embodiments, routine maintenance can be performed based on algorithms that rely upon drilling data fed to the system from an electronic data recording and acquisition system utilizing the wellsite information transfer specification (WITS) protocol. Algorithms can also be used to increase the quality of logged data in mud gas analysis. By using intelligent valve switching, more representative gas values can be recorded and logged during the drilling process, removing false low gas readings resultant from the mud circulating pumps being turned off. Additionally, the condition of the sample for vacuum or pressure changes, temperature, and humidity can be monitored and even affected by the presence of the device or system in a manner that makes the gas sample more agreeable to the instruments of analysis. In various embodiments, as safety and reliability become paramount in industry, the device or system allows for equipment to run unattended safely and dependably.

The present disclosure describes examples of using a series of logical tests based on wellsite drilling data to determine when it is appropriate to automate routine line maintenance. The logical tests can indicate, for example, whether line conditions remain favorable, or whether an emergency maintenance cycle is required. In various embodiments, principles described herein can serve to normalize line maintenance practices between different companies, drilling pads, and field operators.

For illustrative purposes, an example deployment in an oil and gas drill operations is described herein. Particular examples are provided with reference to conveyance of a gas sample from an extractor to and through a device that is potentially placed in a mud-return flow of oil and gas drilling operations. However, it should be appreciated that the same or similar principles can be applied relative to treatment of gas samples for quantitative analysis in any industry. In addition, or alternatively, the same or similar principles may be applied in any field where instrumentation is intended to run for extended periods of time unattended.

FIG. 1 illustrates a system 100 for signaling a start of a sequence such as, for example, a line maintenance or bypass sequence. The system 100 includes a controller 101 and a signaling apparatus 102 that are connected by a data-transfer protocol 103. The data-transfer protocol 103 can be representative of any suitable wired or wireless communication therebetween. In some embodiments, the controller 101 can be a computer that includes, for example, a processor and memory. In some embodiments, the signaling apparatus 102 may be the same physical device as the controller 101, such that the data-transfer protocol 103 can be omitted. The system 100 is also shown to include electrically activated valves 106, 107, 108, 110, 112 and 116 that are powered by timed relays 105, 109, 111 and 115. The electrically activated valves 106, 107, 108, 110, 112 and 116 can be, for example, electrically activated solenoid pressure-control valves with spring return.

The controller 101 is operable to receive and interpret drilling data in various formats, including but not limited to WITS data. In a typical embodiment, the drilling data interpreted by the controller 101 relates to information about drilling operations. In certain embodiments, the controller 101 is programmed with one or more algorithms, or logical conditions, that trigger signaling actions based on the drilling data. Whenever the one or more algorithms or logical conditions so trigger, the controller 101 can send a signal to the signaling apparatus 102 so as to start a sequence.

In general, the signaling apparatus 102 represents a manner of sending gate signals to initiate various timed sequences. For purposes of this patent application, a gate signal refers to any signal used to close a relay or switch and initiate a timer. The gate signals can be sent using general-purpose input/output (GPIO) or any number of integrated controls, for example, on a printed circuit board. The signaling apparatus 102 includes a first negative terminal 104, a second negative terminal 114, and a positive terminal 113. The positive terminal 113 is usable by the signaling apparatus 102 to complete electrical circuits, such as direct current (DC) circuits, using either the first negative terminal 104 or the second negative terminal 114. Connectors 119, which are shown as solid lines in FIG. 1, represent wiring or traces of a printed circuit board that complete a positive side of such electrical circuits. Connectors 118, which are shown as dashed lines in FIG. 1, represent wiring or traces of a printed circuit board that complete a negative side of such electrical circuits. Junctions 117, which are shown as dots in FIG. 1, represent a junction of connectors (e.g., wires or the like) that are continuous. For clarity of illustration, any crossing of dotted and/or dashed lines in FIG. 1 or subsequent Figures that does not include a dot over such crossing is a simple intersection of lines in the drawing, and is not indicative of contact between connections.

According to the example of FIG. 1, the first negative terminal 104 is a source of a signal that initiates a first timed sequence, such as a blowback process, while the second negative terminal 114 is a source of a signal that initiates a second timed sequence, such as a clean-air bypass process. The signaling apparatus 102 acts a switch to close a circuit for each respective timed sequence.

In the example of FIG. 1, the blowback process involves three timed events that are implemented using the timed relays 105, 109 and 111 and the electrically activated valves 106, 107, 108, 110 and 112. As mentioned previously, the first negative terminal 104 can serve as the source of the signal that initiates the blowback process. In this way, the blowback process may be initiated by a gate signal from the first negative terminal 104 to each of the timed relays 105, 109 and 111.

In a typical embodiment, the timed relays 105, 109 and 111 are each individually configured with a time duration that governs its operation. The timed relays 105, 109 and 111 may have different time durations. In an example, the timed relays 105, 109 and 111 can have time durations of seven seconds, forty seconds, and forty-five seconds, respectively. These time durations can also correspond to any other suitable length of time. In general, each timed relay of the timed relays 105, 109 and 111 can be configured such that, when the gate signal from the first negative terminal 104 is applied, the timed relay closes and thereby energizes its output. Once the gate signal from the first negative terminal 104 has been removed, each of the timed relays 105, 109 and 111 begins to count down from its time duration. In a typical embodiment, the timed relays 105, 109 and 111 each de-energizes its output upon expiration of its time duration. In a typical embodiment, the timed relays 105, 109 and 111 close and thereby energize their outputs at the same time, or at approximately the same time, and open and thereby de-energize their outputs at the end of their respective time durations, the lengths of which may configurably vary as noted above.

As a first timed event in the blowback process, the timed relay 105 controls removal of water caught, for example, in a box or device containing the system 100, via timed switching of the electrically activated valves 106, 107 and 108. Upon receipt of input voltage from the signaling apparatus via the first negative terminal 104, the timed relay 105 provides continuous power to the electrically activated valves 106, 107 and 108 for its time duration.

As a second timed event in the blowback process, the timed relay 109 controls a continued purge of a primary sample line via timed switching of the electrically activated valve 110. The electrically activated valve 110 is switched and timed to close upon the expiration of the time duration for the timed relay 109. In a typical embodiment, the electrically activated valve 110 continues to have power during the blowback process. When the time duration for the timed relay 109 ends, the electrically activated valve 110 is no longer powered by the timed relay 109 and switches back to a closed position.

As a third event in the blowback process, the timed relay 111 controls depressurization via timed switching of the electrically activated valve 112. In a typical embodiment, the timed relay 111 causes pressure to flow back through the electrically activated valve 112 away from equipment and into the atmosphere. In the illustrated embodiment, the electrically activated valve 112 is powered by the timed relay 111. When the time duration for the timed relay 111 ends, the electrically activated valve 112 is no longer powered by the timed relay 111 and switches back to a closed position.

In the example of FIG. 1, as described previously, the second negative terminal 114 can serve as the source of the signal that initiates the auxiliary process, such as the clean-air bypass process, which process is initiated by the timed relay 115. In the illustrated embodiment, the electrically activated valve 116 is powered by the timed relay 115, where the timed relay 115 is individually configured with a time duration that governs its operation. In an example, this time duration can be six hours. This time duration can also correspond to any other suitable length of time. When the gate signal gate signal from the second negative terminal 114 is applied, the timed relay 115 closes and thereby powers the electrically activated valve 116. Once the gate signal from the second negative terminal 114 has been removed, the timed relay 115 begins to count down from its time duration. When the time duration for the timed relay 115 ends, the electrically activated valve 116 is no longer powered by the timed relay 115 and switches back to a closed position.

Figure 2:
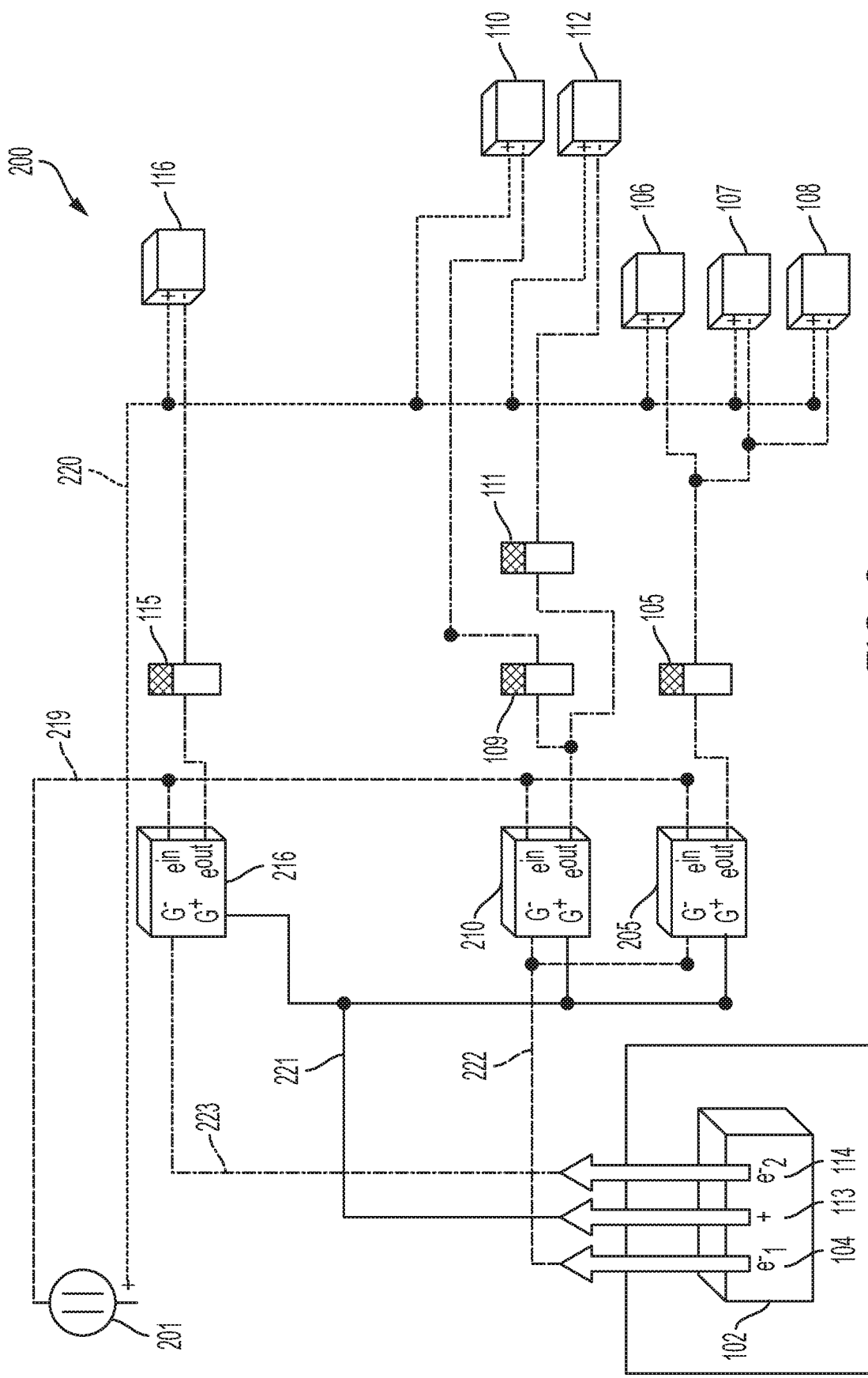
FIG. 2 illustrates an example of a system for delivering electrical power to timed relays and electrically activated valves.

FIG. 2 illustrates an example of a system 200 for delivering electrical power to the timed relays and electrically activated valves shown in FIG. 1. In the illustrated embodiment, the system 200 includes a power supply 201, such as a DC power supply, and relays 205, 210 and 216. The system 200 is further shown to include the signaling apparatus 102, the timed relays 105, 109, 111 and 115 and the electrically activated valves 106, 107, 108, 110, 112 and 116, all of which were described above relative to FIG. 1. Connectors 219, 220, 221, 222 and 223 represent wiring or the like as various dotted, dashed, or solid lines. For illustrative purposes, junctions are shown as dots in FIG. 2, while any crossing of dotted and/or dashed lines in FIG. 2 that does not have a solid dot over it indicates that connectors cross without connecting.

In various cases, the kinds of general outputs typically used to trigger events from printed circuit boards on computing and electronic devices are unable to sufficiently power electrically activated valves such as the electrically activated valves 106, 107, 108, 110, 112 and 116. In certain embodiments, the system 200 can supply sufficient power for the electrically activated valves 106, 107, 108, 110, 112 and 116 via the power supply 201 and the relays 205, 210 and 216.

In the illustrated embodiment, the signaling apparatus 102 is separate and distinct from the power supply 201, the relays 205, 210 and 216 and the timed relays 105, 109 and 115. In various embodiments, the power supply 201, the relays 205, 210 and 216, and the timed relays 105, 109, 111, and 115 may be implemented on a printed circuit board that, in the collective, drives power to the electrically activated valves 106, 107, 108, 110, 112 and 116 and allows current to be increased and voltages to be changed. The power supply 201 may have, for example, five amps or more of available power to drive events. The signaling apparatus 102, in contrast, via the first negative terminal 104 and the second negative terminal 114, may deliver minimal current at a set voltage, as is the general limit to general outputs on microcontrollers and commercial printed circuit board devices.

The relays 205, 210 and 216 may each be, for example, zero-cross relays that have a rated voltage for closing the relay that is between zero and sixty volts DC. The relay 205 completes a circuit by closing, thereby powering the timed relay 105 using power from the power supply 201. The timed relay 105 powers the electrically activated valves 106, 107 and 108 as described previously relative to FIG. 1. In particular, after the gate signal from the signaling apparatus 102 has been sent and removed, such that power no longer passes from the signaling apparatus 102 to the relay 205, the timed relay 105 closes and thereby energizes its output, thus powering the electrically activated valves 106, 107 and 108. The timed relay 105 further begins to count down from its time duration. The timed relay 105 opens and thereby de-energizes its output at the conclusion of its time duration, at which point the electrically activated valves 106, 107 and 108 are no longer powered by the timed relay 105 as described previously. The electrically activated valves 106, 107 and 108 remain unpowered until another event is triggered via a gate signal from the signaling apparatus 102.

In similar fashion, the relay 210 completes a circuit by closing the relay 210, thereby powering the timed relays 109 and 111 using power from the power supply 201. The timed relays 109 and 111 power the electrically activated valves 110 and 112, respectively, as described previously. In particular, after the gate signal from the signaling apparatus 102 has been sent and removed, such that power no longer passes from the signaling apparatus 102 to the relay 210, the timed relays 109 and 111 close and thereby energize their outputs, thus powering the electrically activated valves 110 and 112, respectively. The timed relays 109 and 111 further begin to count down from their respective time durations. The timed relays 109 and 111 individually open and thereby de-energize their outputs at the conclusion of their respective time durations, at which points the electrically activated valves 110 and 112 are no longer powered by the timed relays 109 and 111, respectively, as described previously. The electrically activated valves 110 and 112 remain unpowered until another event is triggered via a gate signal from the signaling apparatus 102.

Similarly, the relay 216 completes a circuit by closing, thereby powering the timed relay 115 using power from the power supply 201. The timed relay 115 powers the electrically activated valve 116 as described previously. In particular, after the gate signal from the signaling apparatus 102 has been sent and removed, such that power no longer passes from the signaling apparatus 102 to the relay 216, the timed relay 115 remains closed for its time duration, thereby energizing its output and powering the electrically activated valve 116. The timed relay 115 opens and thereby de-energizes its output at the conclusion of its time duration, at which point the electrically activated valve 116 is no longer powered by the timed relay 115 as described previously. The electrically activated valve 116 remains unpowered until another event is triggered via a gate signal from the signaling apparatus 102.

Figure 3:
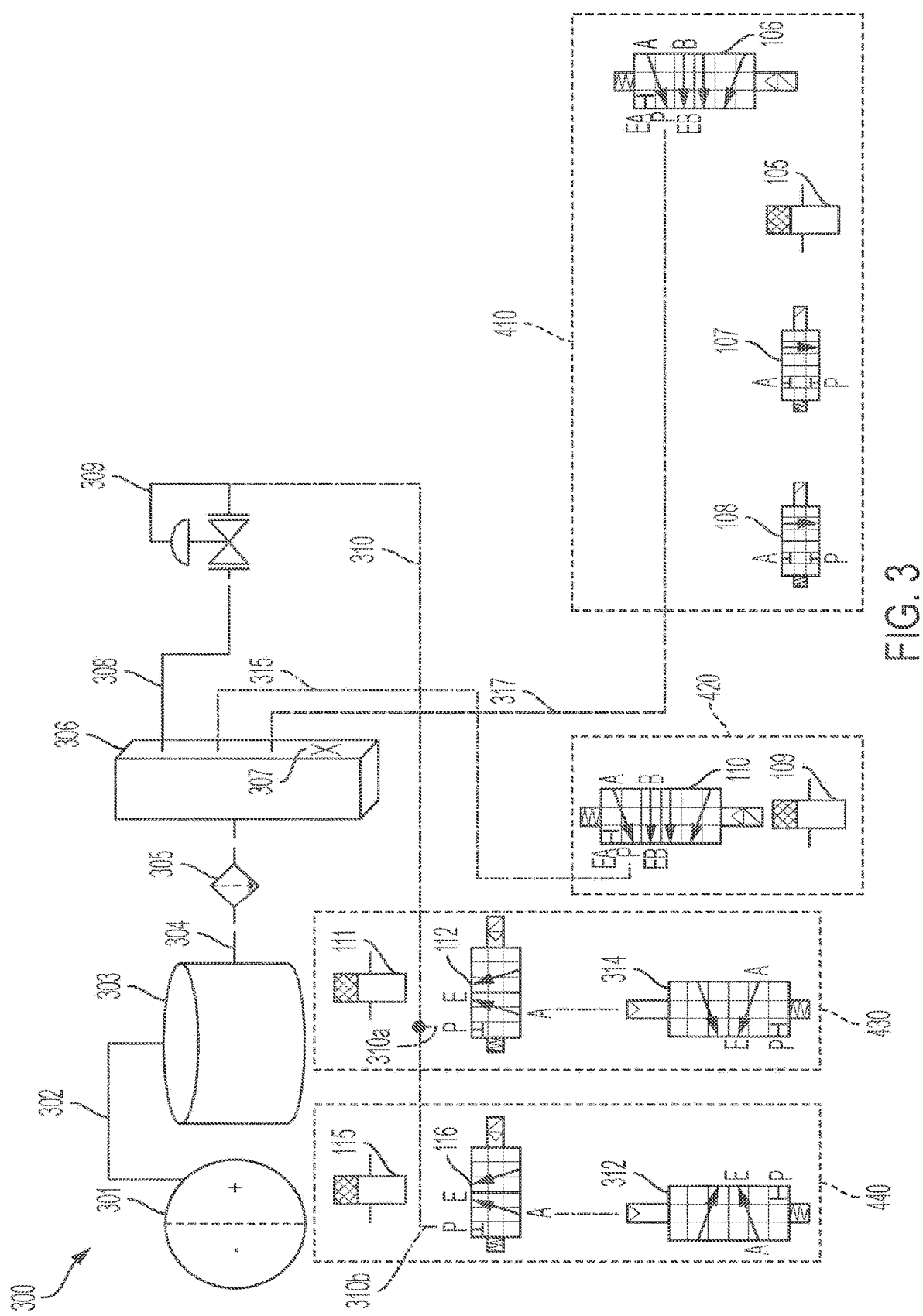
FIG. 3 illustrates an example of a system for delivering compressed air to actuate valves and reverse flow.

FIG. 3 illustrates an example of a system 300 for delivering compressed air to actuate valves and reverse flow. The system 300 includes an air compressor 301, an accumulator 303, a coalescing filter 305, an air manifold 306, and a relieving regulator 309. The system 300 includes connecting hoses and/or tubing 302, 304, 308, 305, 310 and 317 represented as solid, and/or dotted, and/or dashed lines in the same convention as wires have been used in previous figures. The system 300 further includes four valve subsystems, namely, a first valve subsystem 410, a second valve subsystem 420, a third valve subsystem 430 and a fourth valve subsystem 440. Each valve subsystem may contain one or more valves requiring, for example, between 10 and 40 psi, via pneumatically assisted piloting, to switch from a first position to a second position.

The first valve subsystem 410 is controlled by the timed relay 105 and includes the electrically activated valves 106, 107 and 108. When the timed relay 105 is activated and set to count down by the method previously described, the electrically activated valves 106, 107, and 108 switch positions. The electrically activated valves 106, 107 and 108 remain switched to reverse flow through a sample line through the electrically activated valve 106, and to drain, through the electrically activated valves 107 and 108, water and other material that may have collected in a normal-flow situation. Aspects of the sample line and a corresponding flow reversal will be described in greater detail relative to FIGS. 4 and 5A-B.

The second valve subsystem 420 is controlled by the timed relay 109 and includes the electrically activated valve 110. The timed relay 109, when activated and set to count down by the method previously described, powers and causes the electrically activated valve 110 to deliver pressurized air through a connecting sequence to and through the electrically activated valve 106. This connecting sequence will be described in greater detail relative to FIGS. 4 and 5A-B. The air will continue to flow backward until the timed relay 109 opens and the electrically activated valve 110 returns to its closed position.

The third valve subsystem 430 is controlled by the timed relay 111 and includes the electrically activated valve 112 and an air-activated valve 314. The air-activated valve 314 can be, for example, an air-activated, spring-return solenoid valve. The electrically activated valve 112 controls a switching pressure to the air-activated valve 314. When active, the timed relay 111 opens electrically activated valve 112 and thereby switches the air-activated valve 314 to its secondary position. In a typical embodiment, shifting the air-activated valve 314 to its secondary position shuts down sample flow and isolates equipment behind the air-activated valve 314 from high-pressure air. In various embodiments, this step helps protect any pumps, sensors, desiccants and/or analytical instruments behind the air-activated valve 314.

The fourth valve subsystem 440 is controlled by the timed relay 115 and includes the electrically activated valve 116 and an air-activated valve 312. The air-activated valve 312 can be, for example, an air-activated, spring-return solenoid valve. The electrically activated valve 116 controls a switching pressure to the air-activated valve 312. When active, the timed relay 115 opens the electrically activated valve 116 and thereby switches the air-activated valve 312 to its secondary position. In a typical embodiment, the air-activated valve 312 is used to act as a bypass and can be activated, for example, whenever a user wants "clean" air to pass through, behind the air-activated valve 312, to a sample line better illustrated relative to FIG. 4.

In a typical embodiment, the air compressor 301 compresses air, for example, to 80 pound-force per square inch (psi), 125 psi, or more. In a typical embodiment, the compressed air may be considered clean, dry air. Connection 302 connects an output of the air compressor 301 to an accumulator 303. The accumulator is connected, via a connection 304 and a coalescing filter 305, to an air manifold 306 for air distribution. Liquid can be automatically drained through the coalescing filter 305 as the compressed air passes from the air compressor 301 to the air manifold 306. The coalescing filter 305 can further remove, for example, aerosols and dust. In some instances, the coalescing filter 305 may have a relieving air regulator built into itself to adjust pressure down to between 75 psi and 120 psi, for example. In various cases, the air compressor 301, if appropriately sized, can be removed and used for other purposes when deployed on-location.

The air manifold 306 includes a plugged output 307 and three air lines represented by 308, 315 and 317. The air line 308 passes through a relieving regulator 309. The air delivered through the relieving regulator 309 may be reduced, for example, to between 8 and 40 psi. The pressure-reduced air is output from the relieving regulator via air line 310. The air line 310 splits into air lines 310a and 310b to deliver operating pressure through the electrically activated valves 112 and 116, respectively, in the fashion described above. The pressure-reduced air through the lines 310a and 310b actuates the air-activated valves 312 and 314 in the fashion described above.

The air lines 315 and 317 deliver clean and dry air from the air manifold 306 to and through the electrically activated valves 110 and 106, respectively. The air pressure through the electrically activated valve 110 is used to pressure up and drain water through the electrically activated valves 107 and 108, as better illustrated relative to FIGS. 4 and 5B. In a typical embodiment, there is no direct air line to the electrically activated valves 107 and 108 and, therefore, no correspond line is shown in FIG. 3. Rather, in a typical embodiment, the electrically activated valve 110 is connected to the electrically activated valves 107 and 108 via a sample line as better illustrated relative to FIGS. 4 and 5A-B. In a typical embodiment, the air pressure through the electrically activated valve 106 delivers high-pressure, high-velocity air through the sample line to evacuate it of condensed fluids regularly or as desired or appropriate. In various embodiments, the air lines 308, 310, 310a, 310b, 315 and 317 may be implemented, for example, as ¼ inch or greater tubing with a 3/16 inch or greater inside diameter. Such tubing may be rated to handle, for example, 150 psi or greater.

Figure 4:
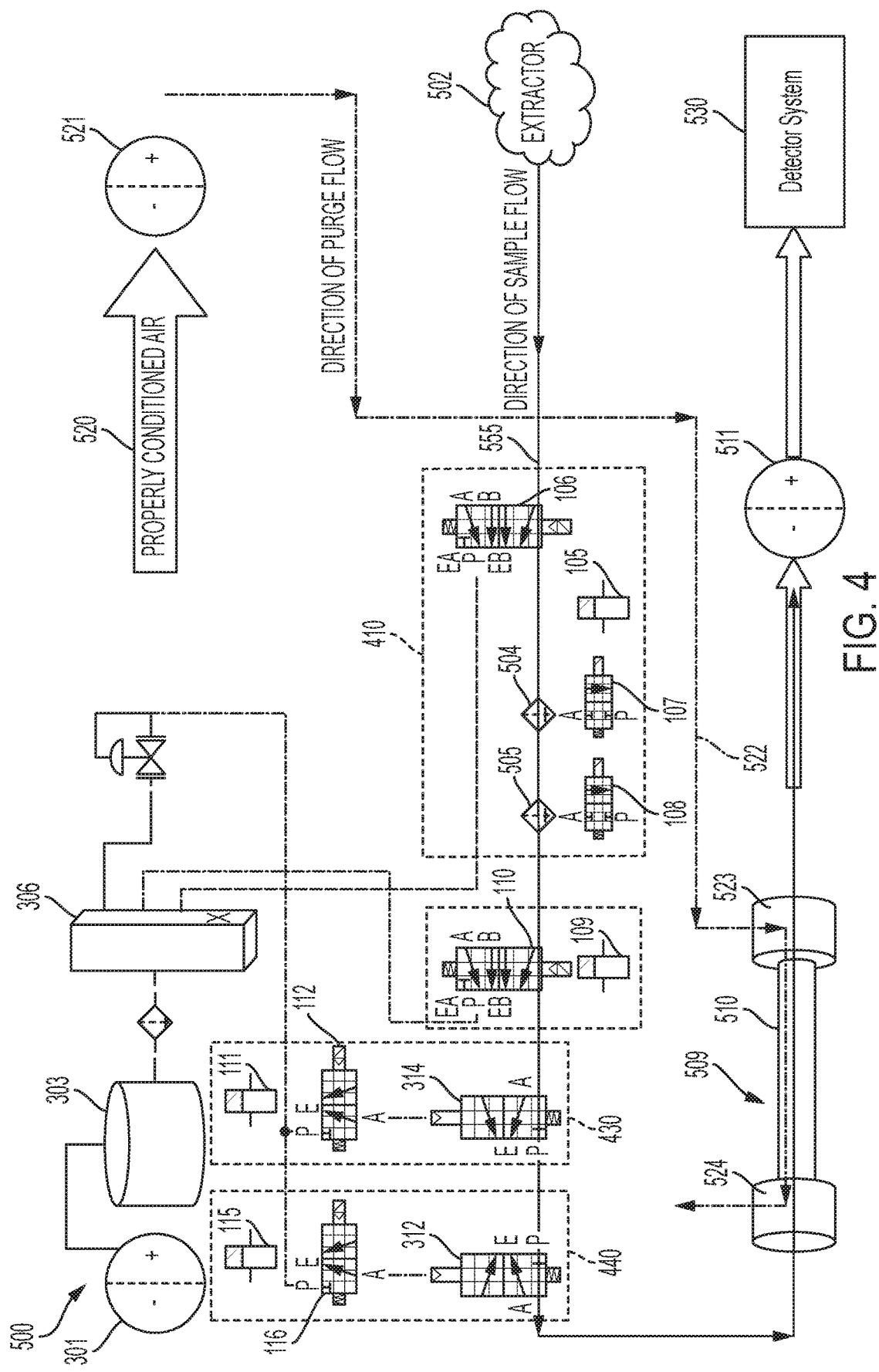
FIG. 4 illustrates an example of a system to remove droplets, particulates and humidity from a gas sample.

FIG. 4 illustrates an example of a system 500 to remove droplets, particulates and humidity from a gas sample. In addition to components previously described relative to FIGS. 1-3, the system 500 includes an external gas extractor 502, a coalescing filter 504, a coalescing filter 505, a hydrophilic membrane 509, a series of hollow ionically charged tubes 510, a sample pump 511, an air pump 521 and a detector system 530.

In various embodiments, the coalescing filter 504 includes a drain, while the coalescing filter 505 includes a particle trap and drain. The coalescing filter 504 and the coalescing filter 505 connect the second valve subsystem 420 through and to all valves of the first valve subsystem 410. The coalescing filter 504 and the coalescing filter 505 can serve to remove water and contaminants as sample flows therethrough. Although the coalescing filter 504 and the coalescing filter 505 are illustrated in conjunction with the first valve subsystem 410 for purposes of illustrating sample flow, it should appreciated that the coalescing filter 504 and the coalescing filter 505 are not part of the first valve subsystem 410.

In one aspect, FIG. 4 illustrates flow of a gas sample through the sample line 555, which line can include any manner of tubing or the like, such as the tubing described previously. In the sample line 555, sample originates from the external gas extractor 502, or other gas source, and passes through the electrically activated valve 106, the coalescing filter 504, the coalescing filter 505, the electrically activated valve 110, the air-activated valve 314 and the air-activated valve 312. Thereafter, the sample flows through hydrophilic membrane 509, via a series of hollow ionically charged tubes 510, to the sample pump 511. In various cases, the sample pump 511 can pass the sample to the detector system 530, which system can include detectors and sensors for analyzing and gathering data related to the sample. In some embodiments, the sample pump 511 can be omitted if, for example, the external gas extractor 502 is under pressure and delivering a pressurized sample passively through differential pressure, provided that the differential pressure does not exceed the ratings of the individual components. In some of these embodiments, a gas regulator may be added to reduce pressure.

In another aspect, FIG. 4 illustrates flow of conditioned air 520 through a purge gas line 522, for example, to remove humidity from the sample. The purge gas line 522 can include any manner of tubing or the like, such as the types of tubing described previously. In a typical embodiment, conditioned air means the air is clean and dehumidified such that the air has a lower relative humidity than the sample. In some embodiments, the conditioned air can be desiccated. The air pump 521 pumps the conditioned air 520 through a hydrophilic membrane 509 at a high volume in a direction opposite the direction of sample flow through the sample line 555. The conditioned air 520 enters the hydrophilic membrane 509 dry at an opening 523. The conditioned air 520 exits the hydrophilic membrane 509 laden with additional water at an opening 524, where the newly wetted air is exhausted to the outside atmosphere. In a typical embodiment, the conditioned air 520 passes through the hydrophilic membrane 509 around an outside of the ionically charged tubes 510, thereby pulling moisture from the hydrophilic membrane 509 at a diffusion-controlled rate. The rate of diffusion may be dependent on several factors including differential in rate of flow, differential air pressure, and differential water content of the conditioned air 520. In this way, the sample enters the hydrophilic membrane 509 wet and exits dry, while the conditioned air 520 enters the hydrophilic membrane 509 dry and exits wet.

Figure 5A:
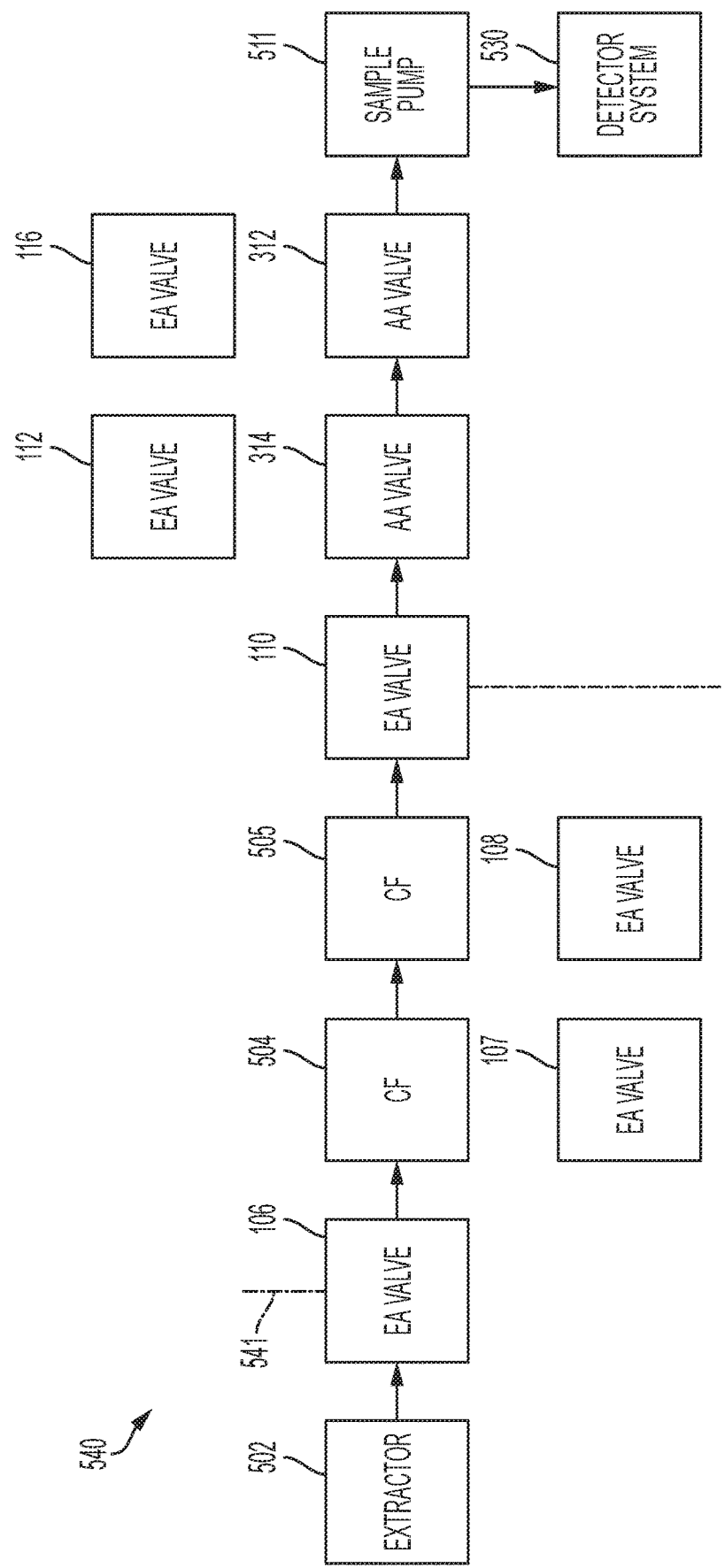
FIG. 5A illustrates example flow in a normal-flow situation.
Figure 5B:
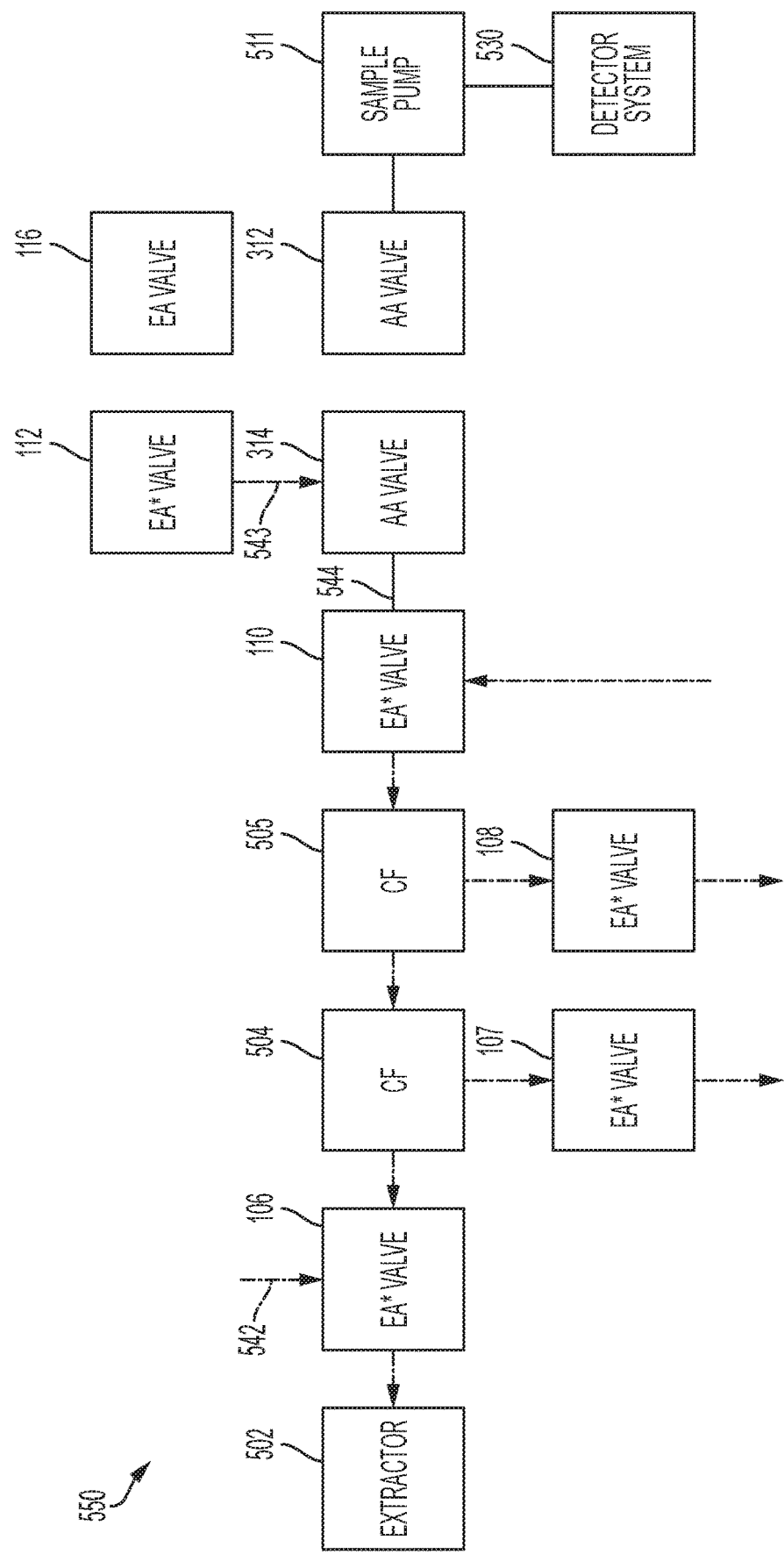
FIG. 5B illustrates example flow in a reverse-flow situation.
Figure 5C:
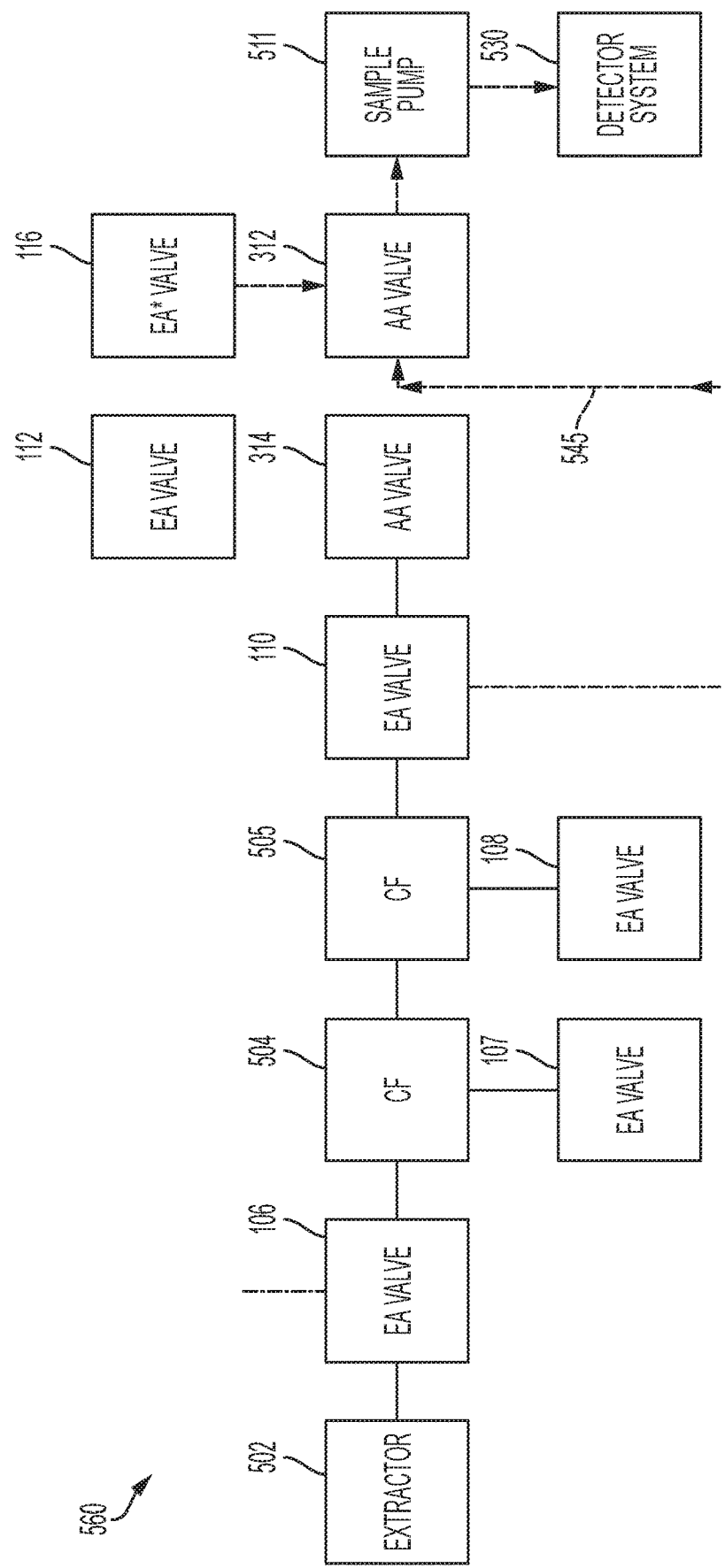
FIG. 5C illustrates example flow in a bypassed-flow situation.
Figure 5D:
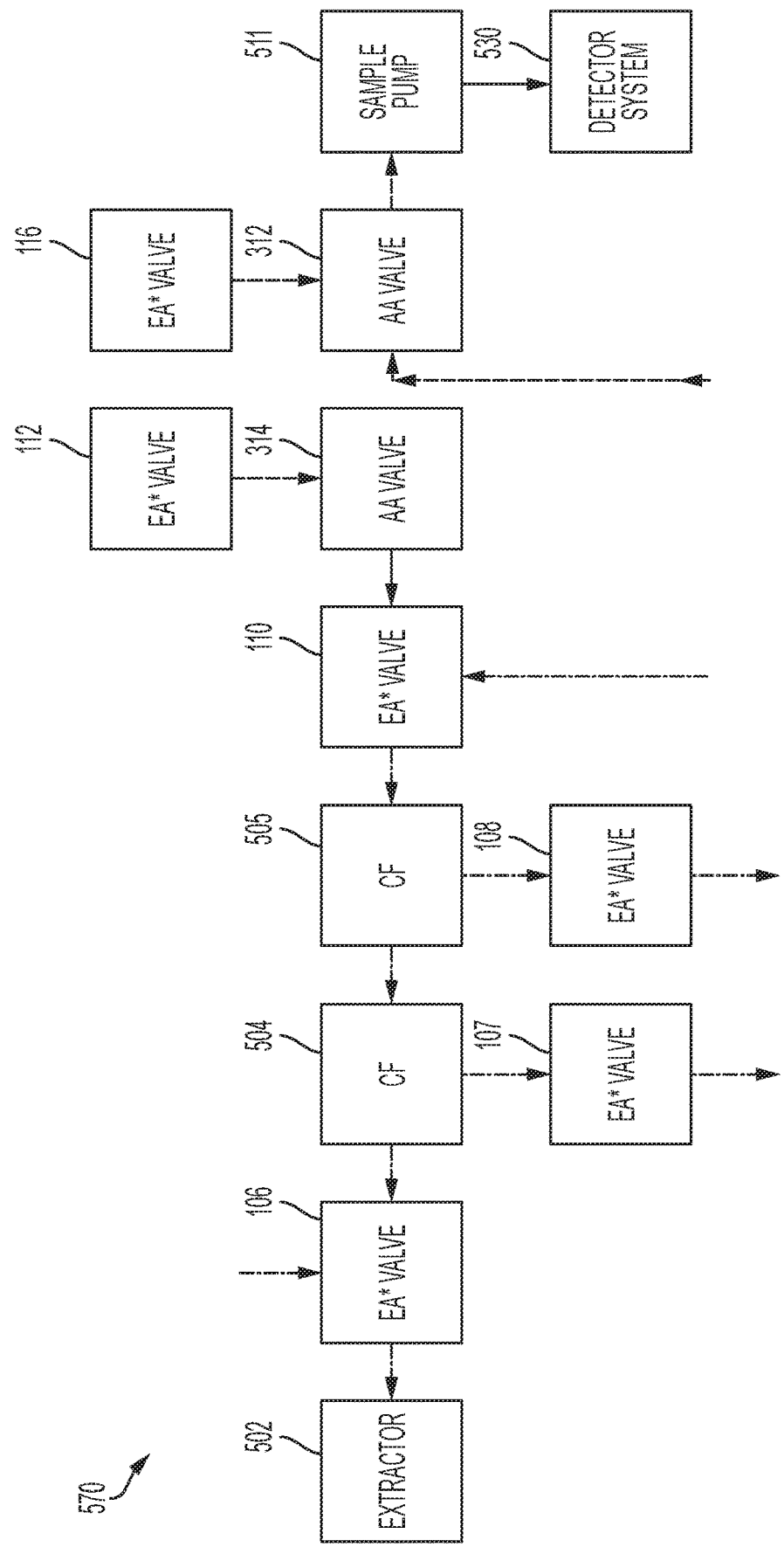
FIG. 5D illustrates example flow in a bypassed and reverse-flow situation.

FIGS. 5A-D illustrate the above-described blowback and bypass processes in more detail. FIG. 5A illustrates example flow in a normal-flow situation 540, while FIG. 5B illustrates example flow in a reverse-flow situation 550. FIG. 5C illustrates example flow in a bypassed flow situation 560. FIG. 5D illustrates an example flow in a bypassed and reverse-flow situation 570.

In FIGS. 5A-D, an "*" represents an electrical current being present at the exact moment a relay, or series of relays, such as the timed relays 105, 109, 111, and 115 for example, are closed. In FIGS. 5A-D, arrows are used to indicate the direction of flow, while the absence of an arrow indicates no flow in any one direction; however, there may be pressurized air present in a dead volume. For FIGS. 5A-D, dashed-dotted lines, such as lines 541 and 542, represent pressurized air meant to flow in reverse to clean and evacuate the lines; dashed lines, such as line 543, represent pressurized air in the system to perform a function, in this case, such as activating a solenoid to close the air-activated valve 314 or the air-activated valve 312, solid lines, such as line 544, represent connections which exist normally and may or may not have air or gas flowing through them. A dotted line, such as line 545, represents the air flow that may be coming into the system when on bypass, not from the gas extractor 502.

In the normal-flow situation 540, the electrically activated valves 106, 107, 108, 110 and 112 and the air-activated valves 312 and 314 are in their initial positions as described previously. In a typical embodiment, these initial positions can correspond to valve positions in the absence of timed events or upon the expiration of an applicable time duration. In the normal-flow situation 540, sample flows from the external gas extractor 502 to the detector system 530 as illustrated.

In the reverse-flow situation 550, timed events such as, for example, the three timed events described above relative to FIG. 1, can cause the electrically activated valves 106, 107, 108, 110 and 112 to be activated. With reference to the first timed event, the electrically activated valve 106 switches positions to reverse flow into the external gas extractor 502 using, for example, air received via the air line 317. Also, as part of the first timed event, the electrically activated valves 107 and 108 can switch positions to allow water from the coalescing filter 504 and the coalescing filter 505, respectively, to drain. With regard to the second timed event, the electrically activated valve 110 switches positions to open to air received via the air line 315, pressure from which facilitates the above-described draining through the electrically activated valves 107 and 108. With regard to the third timed event, the electrically activated valve 112 switches positions to allow operational pressure 562, for example, from the air line 310a shown in FIG. 3, to pass to the air-activated valve 314, which causes the air-activated valve 314 to close and protect systems and components behind it such as, for example, the sample pump 311 and systems and components in the detector system 530. The electrically activated valves 106, 107, 108, 110 and 112 and the air-activated valves 312 and 314 are shown with dashed-line borders in FIG. 5B in order to illustrate that these valves are in their secondary positions. In a typical embodiment, each timed relay will be closed for at least a minimum appropriate period of time in a reverse flow situation so as to not damage sampling or analytical equipment.

In the bypass-flow situation 560, timed events such as for example those described above in FIG. 1, can cause electrically activated valve 116 to be activated. With reference to the timed event, the electrically activated valve 116 switches positions to allow air to pass and activate, for example, a solenoid in the air-activated valve 312. Electrically activated valves are shown in FIG. 5C denoted with an "*" in their symbol boxes. Upon switching, the air activated valve 312 prevents flow from continuing from the external gas extractor 502, and air is pulled from a localized area. In FIG. 5C this is represented by the line 545 flowing in the direction of the sample pump and detector system. In this scenario, air flow from the external gas extractor 502 is discontinued as indicated by a lack of directional arrows coming from the external gas extractor 502.

In a combined sequence, all valves can be activated simultaneously. In a combined reverse-flow and bypassed flow situation 570. FIG. 5D illustrates this situation as it would exist at precisely the time that all relays have been closed via a signaling apparatus as discussed in FIG. 1. In this situation, timed events such as, for example, those described in FIG. 1, can cause electrically activated valves 106, 107, 108, 110, 112, and 116 to be activated. Electrically activated valves as shown in FIG. 5D are denoted with an "*" in their symbol boxes. By simultaneously closing all relays, all valves are either electrically powered, as in valves 106, 107, 108, 110, 112, and 116, or have received an activating pressure, as in valves 312 and 314. Having received either an electrical current or activating pressure each valves switches its position and will remain switched until such a time when the timed relays 105, 109, 111, and 115 no longer supply current to the electrical relays as discussed previously and illustrated in FIG. 1. Once all timed relays have counted down through their timed sequence each relay will open, and the valves will return to their normal position. It is important to note that each timed relay should closed for an appropriate period of time in a reverse a combined flow situation so as to not damage sampling or analytical equipment.

Figure 6:
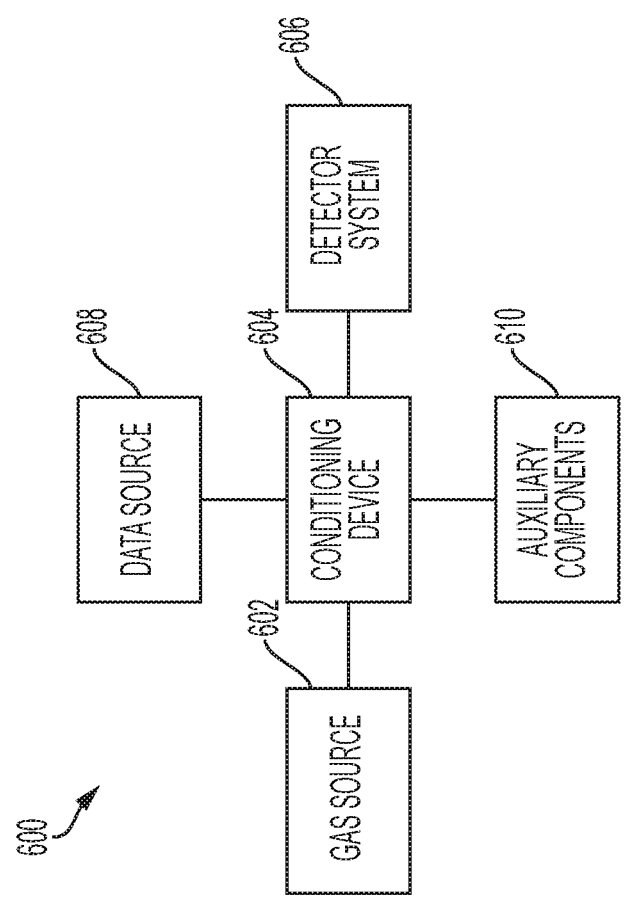
FIG. 6 illustrates an example system that can include an arrangement of various components shown in FIGS. 1-5.

FIG. 6 illustrates an example system 600 that includes an arrangement of various components shown in FIGS. 1-5. The system 600 includes a gas source 602, a conditioning device 604, a detector system 606, a data source 608 and auxiliary components 610. The gas source 602 can include, for example, a gas extractor such as the external gas extractor 502 described relative to FIGS. 5 and 6. The data source 608 can be, for example, a source of drilling data (e.g., WITS data), including but not limited to sensors and computers or systems that compile or record data from such sensors. The detector system 606 can be or include, for example, the detector system 530 described relative to FIG. 5.

The conditioning device 604 can include, for example, controllers, computers, valves, and relays operable to implement various functionality described above relative to FIGS. 1-5. For example, with reference to FIGS. 1-5, the conditioning device 604 can include the controller 101, the signaling apparatus 102, the timed relays 105, 109, 111 and 115, the electrically activated valves 106, 107, 108, 110, 112 and 116, the power supply 201, the relays 205, 210 and 216, the accumulator 303, the coalescing filter 305, the air manifold 306, the relieving regulator 309, the coalescing filter 505, the hydrophilic membrane 509 and the series of hollow ionically charged tubes 510. In various embodiments, the conditioning device 604 interacts with the auxiliary components 610 during its operation. With reference to FIGS. 1-5, the auxiliary components 610 can include, for example, the air compressor 301 and the air pump 521. In some embodiments, some or all of the auxiliary components 610 can be in included within the conditioning device 604.

Figure 7:
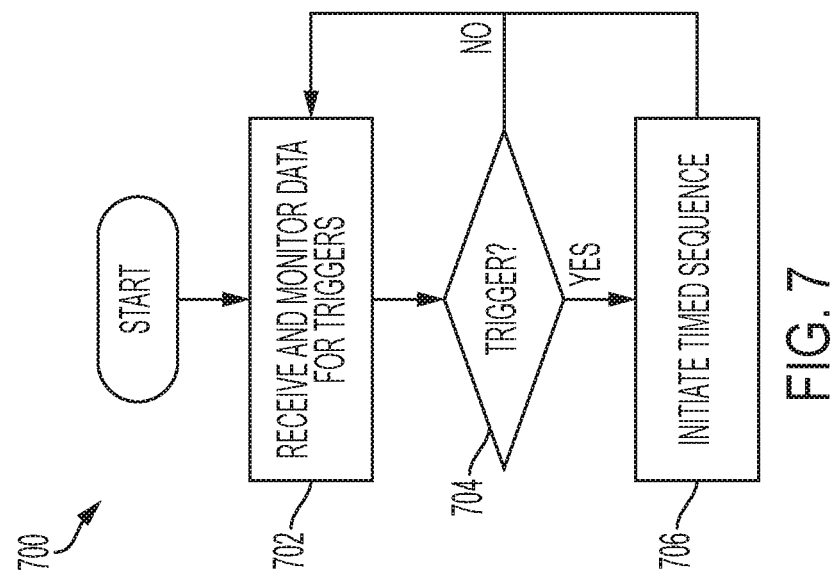
FIG. 7 illustrates an example process for initiating a timed sequence.

FIG. 7 illustrates an example process 700 for initiating a timed sequence.

In various embodiments, the process 700 can be executed by the controller 101 of FIG. 1, the conditioning device 604 of FIG. 6, or another component. Although any number of devices, systems or components can execute the process 700, for clarity of description, the process 700 will be described relative to the conditioning device 604 of FIG. 6.

At block 702, the conditioning device 604 receives and monitors drilling data and other data for triggers of a timed sequence or other operation. The drilling data and other data can be received, for example, from the data source 608 of FIG. 6. Triggers can be specified in the conditioning device 604, for example, via logical tests or algorithms. Example data points that can be used to specify triggers are shown in Table 1 below. Example timed sequences and other operations that can be triggered are shown in Table 2 below. Example scenarios that combine example triggers and example sequences or other operations are shown in Table 3 below. Further examples are described following Table 3.

TABLE 1

Example Data Points for Specification in Triggers

Total Strokes per Minute (SPM) (sum for mud
pumps, e.g., all mud pumps at a location)
Depth of Bit (e.g., feet or meters)
Depth of Hole (e.g., feet or meters)
Sample Line Vacuum Data (e.g., from a sample vacuum transducer
that monitors rate of flow in sample line)
Sample Line Relative Humidity (e.g., via a post-hydrophilic
membrane measurement by a relative humidity sensor)

TABLE 2

Example Timed Sequences or Operations

Initiate blowback process
Initiate bypass process
Terminate bypass process
Empty dropout jars In an example, a trigger for a blowback process can be a kill switch that forces, for example, a blowback upon an expiration of a user-specified interval. In another example, a trigger for a blowback process can be satisfied in response to information indicative of a clog in a sample line. In a more particular example, a trigger for a blowback process can be based on feedback from an onboard vacuum transducer, which relates an amount of drag on a sample line (restriction) to increases in sample vacuum. This situation may indicate that a clog is likely, thus triggering an immediate blowback process. In another more particular example, a trigger for a blowback may be satisfied in response to information indicating a change in rate of flow through a sample line. In some cases, any trigger for a blowback process can be superseded, for example, a minimum interval of time between blowbacks, where blowbacks are not permitted to happen more often than the minimum interval.

In another example, a trigger for a bypass sequence can be based on pumps not circulating in satisfaction of quality criteria. In another example, a trigger for stopping a bypass sequence can be based on a system observation that circulation which previously stopped has resumed. In another example, a trigger for a bypass sequence can be based on an observation that there is a change in flow to indicate displacement of drilling fluid by something else, such as cement. In various embodiments, by initiating a bypass process when pumps are turned off (e.g., not circulating) and turning back to a default position, gas-data quality can be increased as a result of not pulling in gas data for evaluation when not circulating (i.e., not evacuating gas line when not lagging up depth). Further, in various embodiments, initiating a bypass process between blowback processes, when not circulating, can keep unlagged gas from being read when not actively lagging. In other words, there will be less time where gas is registered low at connection depths because pumps were not on and the gas was circulated out of a sample line.

At decision block 704, the conditioning device 604 determines whether criteria for initiating a timed sequence has been satisfied. If not, the process 700 returns to block 702 and executes as described previously. Otherwise, if the conditioning device 604 determines that criteria for initiating a timed sequence has been satisfied, the process 700 proceeds to block 706. At block 706, the conditioning device 604 initiates a timed sequence or other operation in the fashion described above. From block 706, the process 700

TABLE 3

EXAMPLE TRIGGER SCENARIOS

| Scenario | Trigger | Sequence or Operation |
|---|---|---|
| Circulating off bottom | (Hole Depth - Bit Depth) > 0.1 AND Total SPM > 5 | Turn off bypass immediately if on |
| Drilling/Sliding | (Hole Depth - Bit Depth) < 0.1 AND Total SPM > 5 | Turn off bypass immediately if on |
| Connection | (Hole Depth - Bit Depth) < 5 AND Total SPM < 5 | Initiate blowback |
| Pumps off (e.g., a determination that one or more sample pumps are off) | Total SPM < 5 | Initiate bypass (e.g., after 30 seconds) |
| Pumps on (e.g., a determination that one or more sample pumps are on after having been determined to be off) | Total SPM > 5 | Turn off bypass (e.g., immediately) | returns to block 702 and executes as described previously. In various embodiments, the process 700 can execute until terminated by a user or suitable stop criteria is satisfied.

For illustrative purposes, various implementations are described above in terms of timed relays, relays, or the like. In various embodiments, such relays may considered specific examples of "switches." When configured with a time duration, such relays may be considered specific examples of "timed switches." In certain embodiments, various other types of switches can be utilized in place of relays or timed relays. In an example, the functionality of the above-described timed relays can be implemented via metal-oxide-semiconductor field-effect transistor (MOSFET) current drain. In various other examples, the switches can be implemented as software or firmware, for example, that causes signals to be applied and removed in accordance with the above-described time durations. Such software can be implemented in a signal generator and/or in a controller utilizing GPIO configured as output, for example, on a printed circuit board or other type of microcontroller. Other examples will be apparent to one skilled in the art after a detailed review of the present disclosure.

Depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. Although certain computer-implemented tasks are described as being performed by a particular entity, other embodiments are possible in which these tasks are performed by a different entity.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

What is claimed is:

1. A sample conditioning system, comprising:
   one or more valve sub-systems configured to receive a sample via a sample line from a sample source to one or more sample detectors, wherein at least one of the one or more valve sub-systems comprises at least one actuated valve;
   a signal generator in communication with the at least one valve sub-systems, wherein the signal generator is configured to provide a timed signal having a configurable duration;
   a controller communicatively coupled with the signal generator, wherein the controller is operable to:
     receive drilling data from a data source, and responsive to the drilling data satisfying a trigger associated with at least one timed sequence,
     cause the signal generator to provide the timed signal to the one or more valve sub-systems to activate the at least one actuated valve to allow air from an air line to pass to the sample line for the configurable duration.

2. The sample conditioning system of claim 1, wherein:
   the at least one actuated valve is situated in the sample line and configured to receive the sample from the sample source via the sample line; and
   the at least one actuated valve reverses the flow of the sample in the sample line toward the sample source using the air received via the air line.

3. The sample conditioning system of claim 2, wherein:
   the at least one of the one or more valve sub-systems includes a second actuated valve in communication with the signal generator and a coalescing filter situated in the sample line;
   the signal generator is configured to provide a second timed signal having a second configurable duration;
   the second actuated valve configured to allow water deposited by the sample line into the one or more coalescing filters to drain therethrough.

4. The sample conditioning system of claim 3, wherein:
   the at least one actuated valve comprises a plurality of actuated valves; and
   the controller is configured to cause the signal generator to selectively signal the plurality of valves for a third configurable duration to initiate a bypass process while the trigger is satisfied.

5. The sample conditioning system of claim 4, wherein the bypass process results in a bypass of the sample line.

6. The sample conditioning system of claim 4, wherein;
   the first configuration duration, the second configuration duration, and the third configuration duration are different.

7. The sample conditioning system of claim 1, further comprising a set of control valves coupled with the at least one actuated valve, wherein:
   the set of control valves is configured to receive the timed signal from the signal generator,
   the set of control valves changes a configuration of any of the at least one actuated valve in communication with the sample line from a first configuration to a second configuration in a presence of the timed signal, and
   the set of control valves changes the configuration of the at least one actuated valve in communication with the sample line from the second configuration to the first configuration in an absence of the activating signal.

8. The sample conditioning system of claim 1, comprising a hydrophilic membrane situated in the sample line, wherein the hydrophilic membrane is configured to:
   allow sample to flow toward the one or more sample detectors via a plurality of ionically charged tubes situated therein;
   allow purge air to flow therethrough, around an outside space encompassing the plurality of ionically charged tubes, in a direction opposite the flow of the sample, wherein;
     the purge air has a lower relative humidity than gas contained within the plurality of ionically charged tubes, and
     the lower relative humidity allows a diffusion of water through the ionically charged tubes from high concentration to lower concentration.

9. The sample conditioning system of claim 1, wherein the trigger is satisfied in response to a difference between hole depth and bit depth being less than a configurable threshold.

10. The sample conditioning system of claim 1, wherein the trigger is satisfied in response to a difference between hole depth and bit depth being greater or less than a configurable threshold.

11. The sample conditioning system of claim 1, wherein the trigger is satisfied in response to a determination that circulation through the sample conditioning system has substantively ceased.

12. The sample conditioning system of claim 1, wherein the trigger is satisfied in response to a determination that circulation through the sample conditioning system has ceased and then resumed.

13. The sample conditioning system of claim 1, wherein the trigger is satisfied in response to an expiration of a user specified interval indicating that an amount of time has elapsed between specific triggers.

14. The sample conditioning system of claim 1, wherein the trigger is satisfied in response to a clog in the sample line.

15. The sample conditioning system of claim 1, wherein a trigger is satisfied in response to an unexpected change in flow rate through the sample line.

16. The sample conditioning system of claim 1, wherein the signal generator and controller are the same device.

17. The sample conditioning system of claim 1, wherein the at least one actuated valve activated by the timed signal returns to its initial position upon expiration of the configurable duration.

18. A method of automating a sample conditioning system comprising a controller, a signal generator, and a plurality of valves, the method comprising, by the controller:
receiving drilling data from a data source; and
responsive to the drilling data satisfying a trigger associated with a timed sequence, causing a signal from the signal generator to be applied to power at least one actuated valve in a sample line, the powered at least one actuated valve controlling fluid flow through the sample line.

19. The method of claim 18, wherein the powered at least one actuated valve controls the fluid flow by: (1) allowing air from an air line to pass into the sample line, (2) diverting sample flow from the sample line, (3) suspending sample flow from the sample line, or (4) draining water from the sample line.

* * * * *